(12) United States Patent
Taulu et al.

(10) Patent No.: US 7,933,727 B2
(45) Date of Patent: Apr. 26, 2011

(54) METHOD AND DEVICE FOR INTERFERENCE SUPPRESSION IN ELECTROMAGNETIC MULTI-CHANNEL MEASUREMENT

(75) Inventors: Samu Taulu, Helsinki (FI); Juha Simola, Helsinki (FI)

(73) Assignee: Elekta AB (Publ) (SE)

( * ) Notice: Subject to any disclaimer, the term of this patent is extended or adjusted under 35 U.S.C. 154(b) by 218 days.

(21) Appl. No.: 11/912,764

(22) PCT Filed: Apr. 21, 2006

(86) PCT No.: PCT/FI2006/000127
§ 371 (c)(1),
(2), (4) Date: Jun. 24, 2008

(87) PCT Pub. No.: WO2006/114473
PCT Pub. Date: Nov. 2, 2006

(65) Prior Publication Data
US 2008/0294386 A1    Nov. 27, 2008

(30) Foreign Application Priority Data
Apr. 28, 2005  (FI) .................................. 20050445

(51) Int. Cl.
*G01R 29/08* (2006.01)
(52) U.S. Cl. ............. 702/69; 702/71; 702/190; 600/409
(58) Field of Classification Search .................. 702/57, 702/60, 65, 66, 69, 70, 71, 189, 190, 193, 702/197–199; 600/407–410, 420, 422, 430, 600/544; 324/202, 244, 260–261; 370/203–210, 370/335, 342; 375/227, 316, 340, 346, 350; 455/63.1, 67.11, 67.13, 67.14, 114.2, 278.1, 455/296; 340/657, 661–664
See application file for complete search history.

(56) References Cited

U.S. PATENT DOCUMENTS
6,195,576 B1 * 2/2001 John ........................ 600/409
(Continued)

FOREIGN PATENT DOCUMENTS
EP         0966689        12/1999
(Continued)

OTHER PUBLICATIONS
Taulu et al., Clinical Applications of the Signal Space Separation Method, Aug. 2004, Elsevier B.V., pp. 32-37.*
(Continued)

*Primary Examiner* — Eliseo Ramos Feliciano
*Assistant Examiner* — Ricky Ngon
(74) *Attorney, Agent, or Firm* — Studebaker & Brackett PC; Donald R. Studebaker

(57) ABSTRACT

The present invention recognises and eliminates from a biomagnetic measurement signal interferences whose source is disposed in the direct vicinity of an object being measured. The invention utilises the SSS method that can be used to separate from one another the signals associated with the internal and external sources of a set of measurement sensors by calculating two series developments. The sources to be examined in the invention and disposed in the so-called intermediate space produce a component to both of the developments, and can, therefore, be detected by means of an analysis to be performed in a time domain. This division into components can be made using the Principal Component Analysis (PCA), the Independent Component Analysis (ICA) or the Singular Value Decomposition. Finally, the clarified interferences in the intermediate space can be eliminated from the measured signal using, for example, the linear algebraic orthogonal projection.

26 Claims, 2 Drawing Sheets

U.S. PATENT DOCUMENTS

Figure 1:
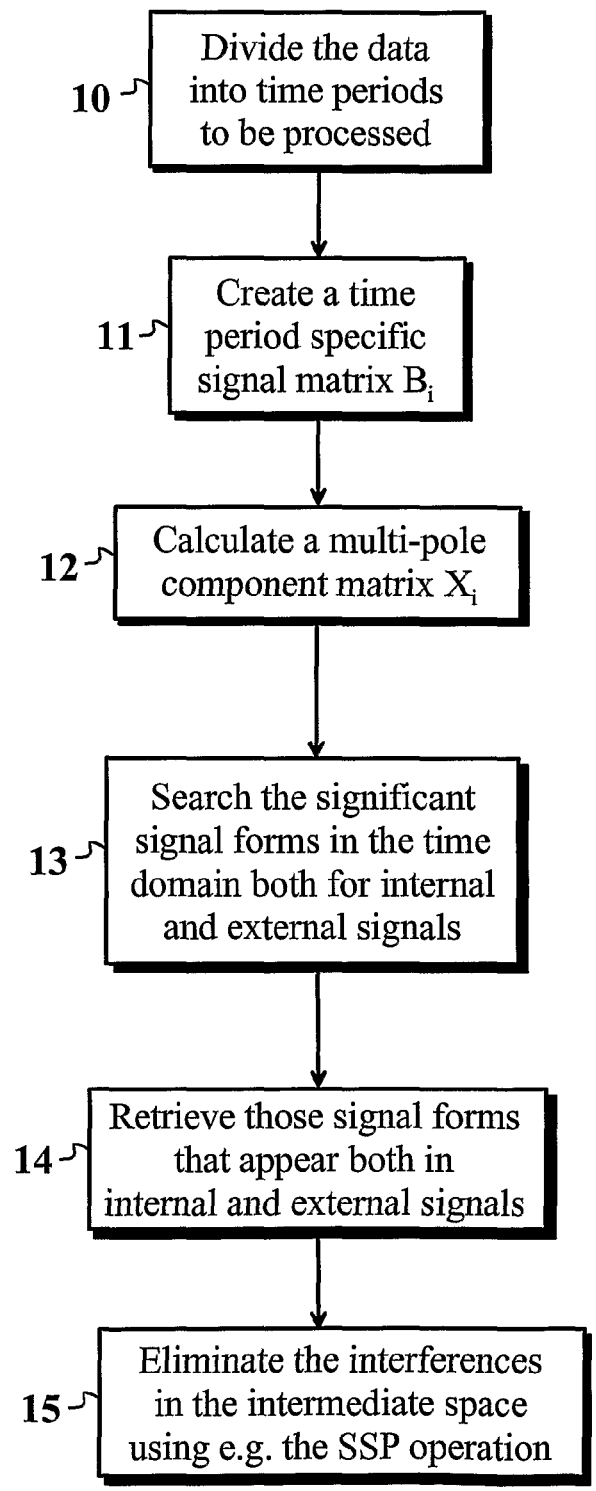

| 6,544,170 | B1 | 4/2003 | Kajihara et al. | |
|---|---|---|---|---|
| 7,254,500 | B2 * | 8/2007 | Makeig et al. | 702/75 |
| 7,263,467 | B2 * | 8/2007 | Sackellares et al. | 702/183 |
| 2003/0032889 | A1 | 2/2003 | Wells | |
| 2005/0055175 | A1 | 3/2005 | Jahns et al. | |
| 2005/0056140 | A1 | 3/2005 | Cho et al. | |
| 2005/0240642 | A1 * | 10/2005 | Parra et al. | 708/400 |

FOREIGN PATENT DOCUMENTS

| WO | WO-2004081595 | 9/2004 |
|---|---|---|
| WO | WO-2005078467 | 8/2005 |

OTHER PUBLICATIONS

Kajola et al., Presentation of Electromagnetic Multichannel Data: The Signal Space Separation Method, Jun. 21, 2005, Journal of Applied Physics, pp. 1-9.*

Volegov et al., Noise-Free Magnetoencephalography Recordings of Brain Function, May 4, 2004, Institute of Physics Publishing, pp. 2117-2127.*

Tonoike et al., Olfactory Cognitive Response Using Odorant Odd-Ball Paradigm by Magnetoencephalography, Sep. 23, 2003, Journal of Temporal Design in Architecture and the Environment, vol. 3, pp. 43-53.*

Diekmann et al., RF-SQUID to DC-SQUID Upgrade of a 28-Channel Magnetoencephalography (MEG) System, Jan. 11, 1996, Measuring Science Technology, vol. 7, pp. 845-852.*

Tonoike et al., Noise Reduction on the Olfactory Neuromagnetic Measurements Using SSP Method, 2001, Osoka National Research Institute, pp. 1-4.*

Taula et al., Suppression of Interference and Artifacts by the Signal Space Separation Method, Brain Topography, vol. 16, No. 4, pp. 269-275, 2004.

Binnie, ":Vagus Nerve Stimulation for Epilepsy: a Review" Seizure, vol. 9, pp. 161-169, 2000.

* cited by examiner

METHOD AND DEVICE FOR INTERFERENCE SUPPRESSION IN ELECTROMAGNETIC MULTI-CHANNEL MEASUREMENT

FIELD OF THE INVENTION

The present invention relates to a novel and advanced method for eliminating from electromagnetic multi-channel measurements such interference signals whose source is disposed very close to the object being measured. In particular, the present invention concerns a novel method for eliminating from multi-channel magnetoencephalographic (MEG) measurements interference signals whose source is disposed at least partly in the region of a patient's head or neck.

BACKGROUND OF THE INVENTION

A device that measures weak biomagnetic signals is very susceptible to the influence of the strong magnetic interferences in its operational environment. This is due to the fact that compared to the biomagnetic signals being measured, the interference signals are even ten million times bigger. Furthermore, the implementation of the interference suppression is made more difficult because the region to be shielded from magnetic interferences is relatively large, tens of centimeters in its diameter.

To make biomagnetic measurements, several methods for protecting measuring devices from interference fields have been developed, which interference fields are many times larger than the interesting signals. In biomagnetic measurements, there is an attempt to achieve as good a signal-to-noise ratio as possible by placing the object being measured, e.g. a patient's head, as close as possible to the sensors of the measuring device while at the same time attenuating the interference sources using, for example, a suitable shielding solution and/or by processing the measured signals with computer algorithms. A straightforward method of shielding is to place a sensitive magnetic measuring device inside a so-called magnetically shielding room which suppresses magnetic fields originating from sources outside the room into about 100-10,000th part.

In addition to this, to achieve magnetic shielding, it is known to use sensors the geometrical structure of which makes them unsusceptible to rather steady magnetic fields originating from distant sources. Magnetic sensors of this kind are called gradiometers. Typically, a shielding factor of about 100-1,000 against external interferences is obtained using them. For example, publication EP0966689 discloses a magnetic gradiometer which is used to measure divergent components of the magnetic field. In particular, the apparatus as shown in publication EP0966689 is capable of measuring a small changing field irrespective of the earth's magnetic field (gradient component of the magnetic field).

Further, the magnetic shielding can be implemented, or it can be improved, using active systems in which the magnetic interference is eliminated by means of a suitable control system in which the interference is measured in the vicinity of the region being shielded by means of a sensor or sensors; and based on this measurement, the interference field is compensated with current-carrying coils that produce a magnetic field that is opposing with respect to the interference. Active magnetic shielding can be used either alone or combined with passive shielding methods such as a magnetic shielding room.

One efficient and dependable manner of eliminating interferences is a so-called SSS method (SSS=Signal Space Separation) because it can be used to separate biomagnetic signals from external interferences merely based on the basic physics of electromagnetic fields and on the geometry of the measuring device. The SSS method has been described e.g. in patent application WO2004081595 and in publication "Suppression of interference and artefacts by the signal space separation method", Taulu et al, Brain Topography, Vol. 16, Number 4, pp. 269-275, 2004.

In the SSS method, a magnetic field measured by a multi-channel MEG device is analysed by examining three different volumes of the measurement geometry. The interesting source is in measurement volume V1; the sensors are in measurement volume V2 outside volume V1. The sources of magnetic interferences and the compensation coils are outside the aforementioned volumes in volume V3. In this examination, the V3 can also be infinite in volume. In the method, the magnetic field produced by the interesting sources disposed in volume V1 is parametrised in volume V2 as a sum of elementary fields, each of them being irrotational, sourceless and finite outside volume V1 so that a presentation of a desired accuracy is achieved for the parametrised magnetic field in volume V2. Similarly, the sum magnetic field produced by the interference fields and compensation coils disposed in volume V3 is parameterised in volume V2 as a sum of elementary fields. The measuring device's signal vectors corresponding to each elementary field are calculated. If a magnetic signal is measured using sensors, then thereafter, the fields produced from sources disposed in different volumes can be separated by calculating the components of the measured signal vector in the basis formed by the signal vectors associated with the elementary fields.

In certain biomagnetic measurements, the source of the interference signal can be disposed at a location where it cannot be classified as an external interference source based on geometric grounds. In that case, one necessitates additional information about the nature of the interference source, such as the exact form of the interference signal in the time domain in order to be able to model and possibly eliminate the interference from the measured data. Advance information required for a satisfactory outcome usually is difficult, or even impossible, to obtain. This kind of interference cannot be suppressed using passive shielding based on magnetic shielding structures, nor can it be suppressed using reference sensors measuring solely external interferences or by using gradiometers or by using the SSS method.

As an example of an application with interference sources disposed very close to the measuring sensors we mention the MEG measurements of such epilepsy patients having the Vagus Nerve Stimulator (VNS) installed for them. The stimulator in question is equipped with electrodes in the neck region that are activated electrically to reduce the number of epileptic fits. The principles of the VNS device have been described, for example, in publication "Vagus nerve stimulation for epilepsy: a review", Binnie, Seizure, Vol. 9, pp. 161-169, 2000. For the time it takes to perform the MEG measurement, the stimulation of the vagus nerve is stopped, but even in that case, the VNS stimulator is activated periodically.

The prior-art technology has several ways of analysing and processing data sets computationally. One such method is the so-called Principal Component Analysis, PCA). The PCA has been used, for example, in publication US2005055175. The PCA enables one to reduce the dimensions of the data set while at the same time keeping as much as possible of the original information. Mutually correlating variables are modified into a set of uncorrelated variables that are sorted into an order. Uncorrelated variables are linear combinations of the original variables. The arranged variables to be obtained as a result are the desired main components.

Another method for processing a data set is the so-called ICA i.e. Independent Component Analysis). The ICA has been used in the prior art, for example, in publication US2005056140. The purpose of the ICA is to divide a complicated data set into independent data sets independent of one another. The ICA is a more efficient method than the PCA, and can be seen as an extension of the PCA. The ICA assumes that the data set to be examined is a linear or non-linear combination of unknown variables. The way the combination is formed is unknown per se, but assuming that the variables are independent of each other it is possible to find out these unknown variables by means of the ICA.

A third known method for finding out the essential components in the time domain from the data is the use of the so-called Singular Value Decomposition (SVD). In the Singular Value Decomposition, the matrix M is decomposed according to the following equation:

$$M = U\Sigma V^* \quad (1)$$

where M is an m*n-matrix whose elements are in region K. U is an m*m-dimensional unitary matrix in region K; V is an n*n-dimensional unitary matrix in region K; V* denotes the conjugate transpose of V; and $\Sigma$ is an m*n-dimensional diagonal matrix whose diagonal elements are non-negative real numbers. In addition, it can also be required that the $\Sigma_{i,i}$ of the diagonal elements must have been sorted into a descending order. In that case Z is unambiguously determined based on X, but U and V are not unambiguous.

The prior art has the disadvantage that the MEG measurements have not presented efficient and universally applicable methods for overcoming the aforementioned problems, which has until now shut certain patient groups out of magnetic measurements.

OBJECTIVE OF THE INVENTION

The objective of the present invention is to overcome the aforementioned disadvantages or at least significantly to alleviate them. One specific objective of the present invention is to disclose a new type of method that can be used to eliminate from biomagnetic measurements such interferences whose source is disposed at such a location where it cannot be clearly classified as an external interference source in geometrical sense.

SUMMARY OF THE INVENTION

The present invention relates to a novel manner of identifying and eliminating from biomagnetic multi-channel measurements such interferences whose source or sources are disposed in the direct vicinity of the object being measured. An interference source such as this can typically be a stimulator which is disposed on the border of the internal and external region of the set of measurement sensors, or in the direct vicinity of this region. Thus, the present invention can be applied, for example, to magnetoencephalographic (MEG) devices that are used to measure weak neuromagnetic signals originating from the brain.

In the invention, the interferences in question are identified independent of the biomagnetic and the actual external interferences, and thereafter the interferences in the time domain are eliminated from the interesting signal. The inventive idea comprises a method for eliminating the interference signals caused by interference sources disposed in the direct vicinity of the sensors of a multi-channel measuring device, and a system for implementing the method in question. The system includes a sensor assembly, a set of feedback coils associated with the sensors, and control means (e.g. a processor) controlling the measuring device and enabling one to perform the calculation operations of the invention. The system can also include a so-called set of reference sensors.

The identification of the interferences is based on the capability of the SSS method (SSS reconstruction) to separate from one another the signals associated with the internal and external sources of the set of sensors. The separation capability is due to the fact that it is possible to present for the aforementioned source sets series developments independent of one another, of which the development that is convergent in the origin is valid for internal sources, and respectively the development that is convergent in the infinity is valid for external sources. The division in question only is valid for sources whose distance from the origin is smaller than the corresponding distance of the sensor that is disposed closest to the origin, or bigger than the distance of the sensor that is disposed farthest from the origin. The signal produced from all the other sources is divided in the origin in a manner to be determined in a complicated manner and among series developments that are convergent in the infinity. In this connection, such interference sources are referred to as sources disposed in the intermediate space, and they correspond, for example, to the magnetic field sources disposed in the direct vicinity of the head or neck surface.

The capability of the present invention to identify interferences in the intermediate space is based on the very fact that after the SSS reconstruction, the signals in question are shown both in internal and external signals, while all the interesting biomagnetic signals are only shown in the internal and all the actual external interferences in the external signals. In the most straightforward manner, the interferences in the intermediate space can be identified by means of an analysis of the time domain because biomagnetic signals and interference signals are independent of one another in respect of time, while interferences in the intermediate space mix together with both the inner and outer signals by creating exactly the same signal in the time domain. Using statistical methods, the signal sets in question can be divided into components in the time domain. If it is detected that one or more internal and external components are correlating with one another with respect of time, then one will know that these signals presented in the time domain inevitably are caused by an interference source disposed in the intermediate space. Thus, interferences in the intermediate space can be suppressed by eliminating signals such as these from a signal associated with internal sources.

In one embodiment of the present invention, prior to the SSS reconstruction, the data measured with sensors is divided into periods of time to be processed. The calculation of the internal and external reconstruction results utilises so-called multi-pole component matrixes calculated based on the matrix of the measured signal.

In another embodiment of the present invention, in conjunction with the reconstruction, the signal components originating from outside the set of sensors are compensated with a so-called residual signal. The calculation of the residual signal can completely omit the signal components originating from outside the set of sensors.

In yet another embodiment of the present invention, it is possible to provide the measurement equipment with a so-called set of reference sensors to measure external interferences. In that case, the signal components originating from outside the set of sensors or the residual signal can be formed from the signals measured by the set of reference sensors.

The division into the components can be performed, for example, using the Principal Component Analysis, PCA), or by retrieving the components independent of the signals (Independent Component Analysis, ICA). A third alternative is to calculate a so-called Singular Value Decomposition (SVD) and to examine the elements of the diagonal matrix to be obtained as a result of the decomposition. The components in the intermediate space can be eliminated using, for example, linear algebraic orthogonal projection (SSP).

The method of the invention can be used as a movement monitoring method or as calibration algorithm of a measuring device.

Compared to the prior art, the present invention can be used to efficiently eliminate the effect of the interference sources disposed in the so-called intermediate space, i.e. those disposed near the measuring sensors, on the measurement of an actual biomagnetic signal.

LIST OF FIGURES

Figure 2:
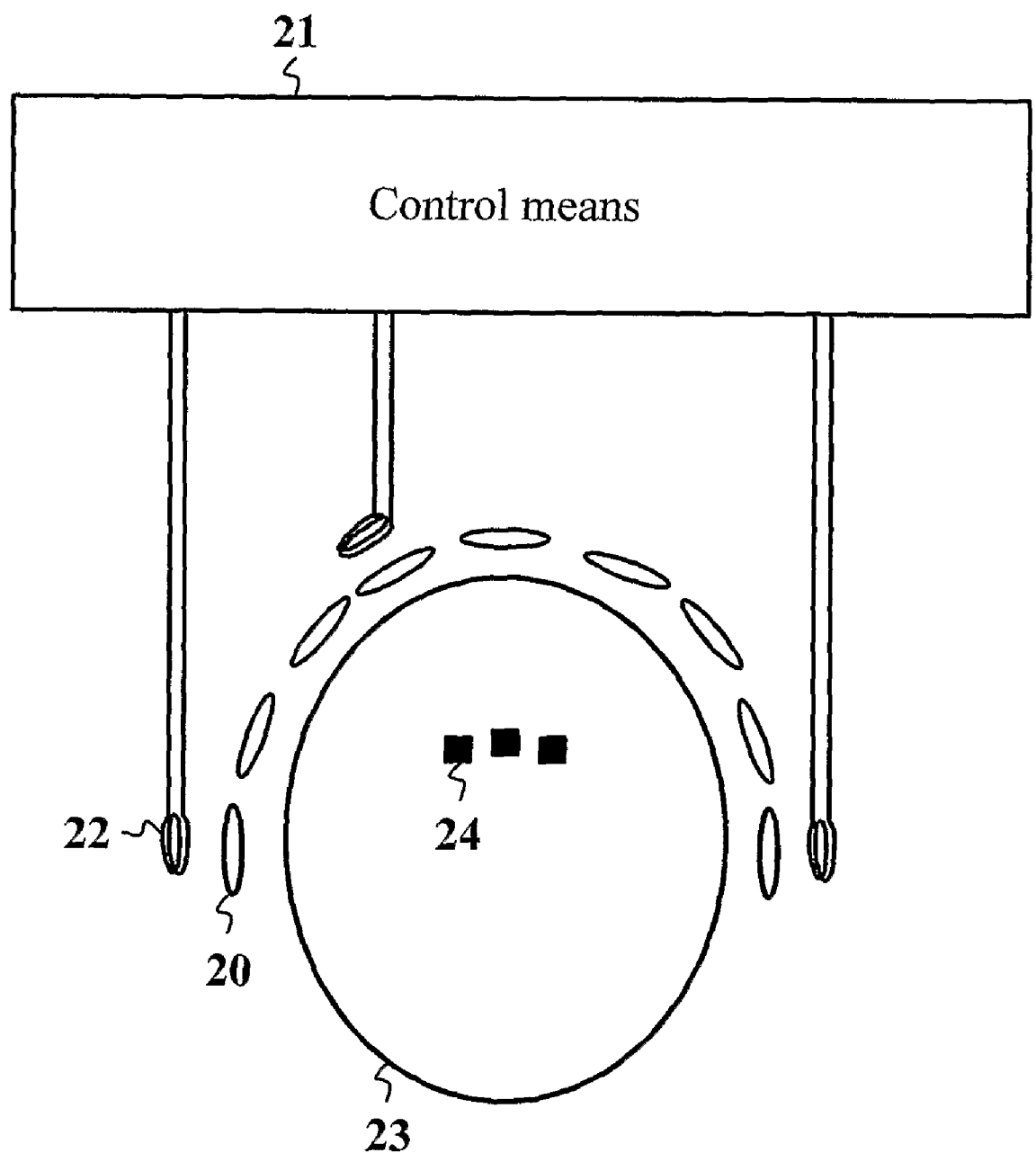

FIG. 1 is a flow chart illustrating one embodiment of the method of the invention; and FIG. 2 illustrates one embodiment of the apparatus of the invention.

DETAILED DESCRIPTION OF THE INVENTION

In the following section, one preferred embodiment of the present invention is shown. In this connection, reference is made to the flow chart shown in FIG. 1. In this mode of carrying out the invention, a mathematical SSS reconstruction of the measured data is performed. The reconstruction finds out both the internal and external multi-pole components. For interference sources that are disposed very close to the sensors, i.e. for those that are disposed in the so-called intermediate space, holds true that they cause signal components both to the external and internal multi-pole components. The interferences in the intermediate space that were found out can be filtered out using a mathematical operation.

At first, the data is divided into suitable periods of time 10, which are processed separately. The periods of time shall be of suitable length to ensure statistical reliability; and, for example, in the MEG, the length should be at least some tens of milliseconds. In particular, it is worth noticing and separating out of the group those periods of time where a significant part of the measurement channels, due to a strong interference, has exceeded the limits of its dynamic operating range, and thus does not give actual information on the magnetic field.

The signals associated with period of time i are denoted with an N×n-dimensional matrix $B_i$ 11, where N denotes the number of channels, and n is the number of samples, which can vary from one period of time to another. In that case, the length in time of the data is $n/f_s$, where $f_s$ denotes the sampling frequency.

After this, each period of time undergoes an SSS reconstruction. At first, the signals are trans-formed into an m×n-dimensional multi-pole component matrix 12:

$$X_i = S^+ B_i \quad (2)$$

where $S^+$ is the pseudo inverse of the SSS basis matrix S. According to the basic idea of the SSS method, signals can be divided into internal and external signals $B_{in,i}$ and $B_{out,i}$, because $X_i$ includes an unambiguous division into the multi-pole components of the inside and outside:

$$X_i = [X_{in,i} X_{out,i}] \quad (3)$$

According to equation (2) there is thus obtained:

$$B_{in,i} = S_{in} X_{in,i} \quad (4)$$

$$B_{out,i} = S_{out} X_{out,i} \quad (5)$$

After the SSS reconstruction, each period of time is performed the Principal Component Analysis (PCA analysis) disclosed in the prior art in a time domain where from the data, the most significant signals 13 in the time domain are searched. The analysis is performed for signals of both the inside and outside, resulting in matrixes $C_{in,i}$ and $C_{out,i}$, of which the former contains an $n_{in,i}$ number and the latter an $n_{out,i}$ number of n-dimensional PCA vectors, which are mutually orthogonal (i.e. independent of each other).

As already mentioned above, the interference sources disposed in the intermediate space inevitably have a share in both the matrix $C_{in,i}$ and $C_{out,i}$, whereas the internal signals only have components in the matrix $C_{in,i}$, and correspondingly, the external signals only have components in the matrix $C_{out,i}$. Thus, as signals disposed in the intermediate space one can classify a vector set such as $C_i = [C_{i1} C_{i2} \ldots C_{ip}]$, which appears substantially both in $C_{in,i}$ and $C_{out,i}$. It can also be said that the desired vector set Ci is an intersection of the signal spaces to be compared. In this manner, the signals representing the interferences in the intermediate space are found out 14. It must be noted that the number p of said vectors can vary from one period of time to another.

After the PCA analysis, the interference in the intermediate space can be eliminated 15, for example, by performing in the time domain an SSP operation (Signal Space Projection), in which the internal signal vectors are in this case projected against the known interference sub-space, i.e. Ci to a perpendicular plane. Mathematically, this can be presented as follows:

$$B_i = [P_i B_{in,i}^T]^T \quad (6)$$

and $$P_i = I - C_i C_i^T \quad (7)$$

where $B_i$ denotes a signal purified from interferences; $P_i$ is a projection operator; T denotes transpose and I denotes a unit matrix.

One alternative way at the step of calculating equations (4) and (5) is to compare the internal signals $B_{in,i}$ with the residual $B_{res,i}$. The residual is determined as follows:

$$B_{res,i} = B_i - (B_{in,i} + B_{out,i}) \quad (8)$$

By searching the significant signal forms in the time domain for the internal signals and for the calculated residual it is possible to obtain the matrixes $C_{in,i}$ and $C_{res,i}$. By comparing these, it is possible to find out the vector set $C_i$ of the interferences disposed in the intermediate space.

One embodiment of the present invention comprises that in the calculation, the external signals $B_{out,i}$ are left out. Thus, in the SSS reconstruction, just the internal signals and the residual are calculated. It must be noted that in that case the residual is of the form:

$$B_{res,i} = B_i - B_{in,i} \quad (9)$$

For the internal signals and the calculated residual (9) it is further possible to perform the analysis of the aforementioned components, and the vector sets $C_{in,i}$ and $C_{res,i}$ thus obtained can be compared with one another.

One embodiment of the present invention comprises that the method utilises, in addition, the set of reference sensors. In that case, the actual measurement sensors are disposed near the measurement object (e.g. a head), and farther, as seen from the measurement object, are disposed reference sensors that are only used to measure external big-amplitude interferences. In that case, the external signals $B_{out,i}$ or $B_{res,i}$ can be formed from the signals measured by the set of reference sensors. In that case, to find out the external signals, one does not necessitate any SSS reconstruction or any other signal processing. One alternative is then to compile the internal signals $B_{in,i}$ from the unprocessed signals measured by the actual signal sensors.

Instead of the Principal Component Analysis (PCA), in the search of the significant signal forms in the time domain, it is possible to use the ICA and SVD methods mentioned in the prior-art part. Similarly, the analysis of the independent variables and the use of the singular value decomposition can also find out the significant signal forms in the time domain for the comparison.

FIG. 2 is an example illustrating an MEG apparatus (magnetoencephalography) that can be used to measure a neuromagnetic signal. The device consists of a sensor assembly 20 (including nine sensors in the example of the figure) surrounding the head of a person being monitored and of electronics 21 controlling the operation of the measuring device. The system has been illustrated as a simplified figure as seen from above.

Associated with each sensor of the device is a small-sized feedback coil 22, by means of which the control means 21 run the sensor 20 in a so-called flow-locked state. This means that the control means 21 introduce current into the feedback coil 22, the field produced by which current cancels in the sensor 20 the field entering that sensor and originating from a source disposed in the object being monitored 23. The voltage necessary to obtain this current, thus comparable to the magnetic effect passing through the sensor 20 from the source 23, is the measurement signal given by the channel in question. All conventional MEG devices have been implemented according to this principle.

The feedback coils 22 are sensor-specific. The coils are so small and so positioned that the field produced by them only causes an effect in the sensor of each coil's own. We can think that the sensor 20 and the feedback coil 22 together form the component functioning as a physical sensor. In an arrangement such as this, all the measurement channels naturally react to the magnetic fields originating from both the object being measured 23 and the external interference sources.

In the example as shown in FIG. 2, as the interference sources disposed in the vicinity of the measurement region of the sensors 20 function three electrodes 24, which can act as the stimulator of the vagus nerve in the region of a patient's neck. In that case, the region of a patient's neck is considered to be included in the so-called intermediate space when the measuring sensors 20 are disposed about a patient's head 23. Thus, the present invention observes interferences caused by electrodes 24 and filters them out from the signal measured by sensors 20, in a manner as described above.

One application of the present invention includes the use as a movement monitoring method. This can be implemented, for example, so that the outer surface of the head is provided with signal transmitters representing sources disposed in the intermediate space. These signal transmitters can be, for example, small coils. If the head is moving, then it shows as signals produced by these sources in the vector set $C_i$. Thus, by examining the vector set it is possible to observe and model the movement.

Another application of the present invention is the use as a calibration algorithm. An inaccurate calibration of the measurement system causes erroneously signal components deviating from zero into the matrix $C_i$, although there would not be any signal sources in the intermediate space. In other words, the device can be calibrated by setting the calibration parameters of the device to values by which the signal shown in the $C_i$ is minimised. Thus, the calibration can be performed in this manner provided that it is known that during the calibration measurement there are no sources in the intermediate space.

The method of the present invention can be implemented as a computer program, a circuit solution or as a combination of these.

The invention is not limited merely to the examples of its embodiments referred to above; instead many variations are possible within the scope of the inventive idea defined by the claims.

The invention claimed is:

1. A method for eliminating interferences in an intermediate space, comprising a set of sensors of a multi-channel measuring device, the method comprising:
   measuring signals using at least one magnetic sensor;
   reconstructing the signal components originating from the inside and outside of the set of sensors based on the measured signals using Signal Space Separation (SSS) method;
   comparing the reconstruction result of the inside to the reconstruction result of the outside based on a statistical analysis of time series;
   recognising interferences in the intermediate space caused by interference sources disposed in the direct vicinity of the set of sensors by the fact that signals representing the interferences in the intermediate space affect at least one signal component in the reconstruction result of both the inside and outside of the set of sensors; and
   eliminating the signals representing the interferences in the intermediate space from the measured signals.

2. The method as defined in claim 1, further comprising:
   prior to the comparison, performing a Principal Component Analysis of both the inside and outside reconstruction results; and
   recognising the interference signals by examining the similarity of the results obtained by the Principal Component Analysis.

3. The method as defined in claim 1, further comprising:
   prior to the comparison, performing an Independent Component Analysis of both the inside and outside reconstruction results; and
   recognising the interference signals by examining the similarity of the results obtained by the Independent Component Analysis.

4. The method as defined in claim 1, further comprising:
   prior to the comparison, performing a Singular Value Decomposition of both the inside and outside reconstruction results; and
   recognising the interference signals by examining the values of the diagonal elements of the matrix $\Sigma$ to be obtained as a result of the decomposition.

5. The method as defined in claim 1, further comprising:
   prior to the reconstruction, dividing the measured data into periods of time to be processed.

6. The method as defined in claim 1, wherein in the SSS method, a magnetic field that was registered using a multi-channel measuring device is analyzed in a geometry in which the interesting source is disposed in measurement volume V1; the sensors measuring the field or the components thereof in volume V2 outside volume 1; and the sources of the magnetic interferences as well as the actuators in volume V3 outside volume V1 and volume 2, which volume 3 can be infinite, further comprising:

parametrising the magnetic field produced by the interesting sources disposed in volume V1 in volume V2 as a sum of elementary fields, each of them being irrotational, sourceless and finite outside volume V1 so that a presentation of a desired accuracy is achieved for the parametrised magnetic field in volume V2;

parametrising the sum magnetic field produced by the interference sources and the compensating actuators disposed in volume V3 in volume V2 as a sum of elementary fields, each of them being irrotational, sourceless and finite outside volume V3 so that a presentation of a desired accuracy is achieved for the parametrised magnetic field in volume V2;

calculating the measuring device's signal vector corresponding to each elementary field;

measuring the magnetic signal using sensors; and separating the fields produced from sources disposed in different volumes by calculating the components of the measured signal vector in the basis formed by the signal vectors associated with the elementary fields.

7. The method as defined in claim 1, further comprising:
creating a signal matrix for each period of time being examined; and
calculating, in the SSS method, for each period of time being examined, multi-pole component matrices of the inside and outside by means of the signal matrix and a basis matrix provided by the SSS method.

8. The method as defined in claim 1, further comprising:
replacing, in the reconstruction, the signal components originating from the outside of the set of sensors with a residual signal.

9. The method as defined in claim 1, further comprising:
forming a residual signal by omitting the signal components originating from the outside of the set of sensors from the calculation of the residual signal.

10. The method as defined in claim 1, comprising:
providing a multi-channel measuring device with a set of reference sensors to measure external interferences; and
forming the signal components originating from the outside of the set of sensors or a residual signal from the signals measured by the set of reference sensors.

11. The method as defined in claim 1, further comprising:
eliminating the recognised interference signals from the measured signal using the SSP method.

12. The method as defined in claim 1, wherein the method is used as a movement monitoring method.

13. The method as defined in claim 1, wherein the method is used as a calibration algorithm.

14. The method as defined in claim 1, wherein the method is used in a magnetoencephalographic device (MEG).

15. A system for eliminating interferences in an intermediate space, the system comprising:
a set of sensors of a multi-channel measuring device including at least one magnetic sensor configured to measure signals;
a feedback coil coupled to each magnetic sensor;
control means configured to control the measuring device;
control means configured to reconstruct the signal components originating from the inside and outside of the set of sensors based on the measured signals using Signal Space Separation (SSS) method;
control means configured to compare the reconstruction result of the inside to the reconstruction result of the outside based on a statistical analysis of time series;
control means configured to recognise interference in the intermediate space caused by interference sources disposed in the direct vicinity of the set of sensors by the fact that signals representing the interferences in the intermediate space affect at least one signal component in the reconstruction result of both the inside and outside of the set of sensors; and
control means configured to eliminate the signals representing the interferences in the intermediate space from the measured signals.

16. The system as defined in claim 15, further comprising:
control means for performing a Principal Component Analysis of both the inside and outside reconstruction results prior to the comparison; and
control means for recognising the interference signals by examining the similarity of the results given by the Principal Component Analysis.

17. The system as defined in claim 15, further comprising:
control means for performing an Independent Component Analysis of both the inside and outside reconstruction results prior to the comparison; and
control means for recognising the interference signals by examining the similarity of the results given by the Independent Component Analysis.

18. The system as defined in claim 15, further comprising:
control means for performing a Singular Value Decomposition of both the inside and outside reconstruction results prior to the comparison; and
control means for recognising the interference signals by examining the values of the diagonal elements of the matrix $\Sigma$ to be obtained as a result of the decomposition.

19. The system as defined in claim 15, further comprising:
control means for dividing the measured data into periods of time to be processed, prior to the reconstruction.

20. The system as defined in claim 15, wherein in the SSS method, a magnetic field that was registered using a multi-channel measuring device is analysed in a geometry in which the interesting source is disposed in measurement volume V1; the sensors measuring the fields or its components in volume V2 outside volume V1; and the sources of the magnetic interferences as well as the actuators in volume V3 outside volume V1 and V2, which volume V3 can be infinite, the control means being arranged to:
parameterise the magnetic field produced by the interesting sources disposed in volume V1 as a sum of elementary fields, each of them being irrotational, sourceless and finite outside volume V1 so that a presentation of a desired accuracy is achieved for the parametrised magnetic field in volume V2;
parameterise the sum magnetic field produced by the interference sources and the compensating actuators disposed in volume V3 as a sum of elementary fields, each of them being irrotational, sourceless and finite outside volume V3 so that a presentation of a desired accuracy is achieved for the parametrised field in volume V2;
calculate the measuring device's signal vector corresponding to each elementary field;
measure the magnetic signal using sensors; and
separate the fields produced from sources disposed in different volumes by calculating the components of the measured signal vector in the basis formed by the signal vectors associated with the elementary fields.

21. The system as defined in claim 15, comprising:
control means for creating a signal matrix for each period of time being examined; and
control means for calculating multi-pole component matrices of the inside and outside by means of the signal matrix and a basis matrix of the SSS method for each period of time being examined in the SSS method.

22. The system as defined in claim 15, further comprising:
control means for replacing the signal components originating from the outside of the set of sensors with a residual signal in the reconstruction.

23. The system as defined in claim 22, further comprising:
control means for forming a residual signal by omitting the signal components originating from the outside of the set of sensors from the calculation of the residual signal.

24. The system as defined in claim 15, further comprising:
a set of reference sensors added to a multi-channel measuring device for measuring external interferences; and
control means for forming signal components originating from the outside of the set of sensors or a residual signal from the signals measured by the set of references sensors.

25. The system as defined in claim 15, further comprising:
control means for eliminating the recognised interference signals from the measured signal using the SSP method.

26. The system as defined in claim 15, wherein the set of sensors, the feedback coils and the control means function as parts of a magnetoencephalographic (MEG) device.

* * * * *